(12) United States Patent
Nguyen et al.

(10) Patent No.: US 8,648,023 B2
(45) Date of Patent: Feb. 11, 2014

(54) PROCESS FOR INHIBITING DYED HAIR FIBERS FROM LOSING THEIR COLOR DURING SHAMPOOING

(75) Inventors: Nghi Van Nguyen, Edison, NJ (US); David W. Cannell, New Hope, PA (US); Cynthia Chong Espino, Princeton, NJ (US); Katherine Natalie Barger, Cranford, NJ (US)

(73) Assignee: L'Oréal (FR)

( * ) Notice: Subject to any disclaimer, the term of this patent is extended or adjusted under 35 U.S.C. 154(b) by 0 days.

(21) Appl. No.: 13/537,542

(22) Filed: Jun. 29, 2012

(65) Prior Publication Data

US 2012/0269756 A1 Oct. 25, 2012

Related U.S. Application Data

(63) Continuation of application No. 12/785,839, filed on May 24, 2010, now Pat. No. 8,236,743, which is a continuation of application No. 11/280,371, filed on Nov. 16, 2005, now abandoned.

(51) Int. Cl.
*C11D 7/36* (2006.01)
*C11D 3/37* (2006.01)

(52) U.S. Cl.
USPC ........... 510/122; 510/119; 510/123; 510/124; 510/125; 510/130; 510/436; 510/466; 510/467; 510/499

(58) Field of Classification Search
USPC ......... 510/119, 122, 123, 124, 125, 130, 436, 510/466, 467, 499
See application file for complete search history.

(56) References Cited

U.S. PATENT DOCUMENTS

| | | | |
|---|---|---|---|
| 5,070,171 A | 12/1991 | O'Lenick, Jr. | |
| 5,093,452 A | 3/1992 | O'Lenick, Jr. | |
| 5,149,765 A | 9/1992 | O'Lenick, Jr. | |
| 5,248,783 A | 9/1993 | O'Lenick | |
| 5,739,371 A | 4/1998 | O'Lenick, Jr. | |
| 6,451,747 B1 | 9/2002 | Decoster et al. | |
| 6,482,400 B1 * | 11/2002 | Collin | 424/70.6 |
| 6,685,926 B2 | 2/2004 | Hehner et al. | |
| 8,128,917 B2 | 3/2012 | Cannell et al. | |
| 2003/0157035 A1 * | 8/2003 | Chaudhuri | 424/59 |
| 2003/0165453 A1 | 9/2003 | Nguyen et al. | |
| 2004/0062737 A1 * | 4/2004 | Nguyen et al. | 424/70.12 |
| 2004/0063592 A1 * | 4/2004 | Nguyen et al. | 510/124 |
| 2004/0241114 A1 | 12/2004 | Gupta | |
| 2006/0286057 A1 * | 12/2006 | Cannell et al. | 424/70.12 |
| 2007/0107141 A1 | 5/2007 | Nguyen et al. | |
| 2007/0110690 A1 | 5/2007 | Nguyen et al. | |
| 2007/0110691 A1 | 5/2007 | Nguyen et al. | |

FOREIGN PATENT DOCUMENTS

| | | |
|---|---|---|
| DE | 197 35 865 | 4/1999 |
| EP | 1 238 648 | 9/2002 |
| EP | 1 302 195 | 4/2003 |
| EP | 1 312 341 | 5/2003 |
| EP | 1 402 881 A1 | 3/2004 |
| EP | 1 733 717 A1 | 12/2006 |
| WO | 93/25179 | 12/1993 |

OTHER PUBLICATIONS

CTFA International Cosmetic Ingredient Dictionary and Handbook, 8th ed. vol. 2, 2000, pp. 1701-1703.

* cited by examiner

*Primary Examiner* — Charles Boyer
(74) *Attorney, Agent, or Firm* — Lerner, David, Littenberg, Krumholz & Mentlik, LLP

(57) ABSTRACT

A process for inhibiting dyed hair fibers from losing their color during shampooing involving contacting the dyed hair fibers with a composition containing: (a) at least one polyamine compound having at least two amino groups; (b) at least one anionic silicone; and (c) optionally, at least one surfactant, and wherein (a) is present in the composition in an amount sufficient to inhibit the dyed hair fibers from losing their color during shampooing.

15 Claims, No Drawings

PROCESS FOR INHIBITING DYED HAIR FIBERS FROM LOSING THEIR COLOR DURING SHAMPOOING

CROSS-REFERENCE TO RELATED APPLICATIONS

This application is a continuation of U.S. application Ser. No. 12/785,839, filed May 24, 2010, which is a continuation of U.S. patent application Ser. No. 11/280,371, filed on Nov. 16, 2005, the disclosures of which are incorporated herein by reference.

BACKGROUND OF THE INVENTION

The present invention relates to a process for inhibiting dyed hair fibers from losing their color during shampooing. The process involves contacting the hair fibers with a composition containing at least one polyamine compound having at least two amino groups and at least one anionic silicone.

There are essentially two ways in which keratin fibers may be dyed: "permanent" dyeing and "semi-permanent" dyeing.

The first, also known as oxidation dyeing, uses "oxidation" dye precursors, which are colorless or weakly colored compounds. Once mixed with oxidizing products, at the time of use, these precursors lead to colored compounds and dyes via a process of oxidative condensation. In this case, the colorations obtained are generally very colorfast and strong.

The second, also known as direct dyeing, uses direct dyes, which are nonionic or ionic dyes and colored compounds capable of producing a more or less pronounced change of the natural color of the hair, resistant to shampoo-washing several times. These dyes may or may not be used in the presence of an oxidizing agent.

In contrast with oxidation dye precursors, a direct dye is a relatively voluminous molecule that does not penetrate easily into the core of the fiber. Consequently, even though considerable progress has been made in this field, the phenomenon of bleeding of the coloration, i.e., color loss, during shampooing is still non-negligible, even if the dye(s) used is (are) chosen from cationic species. Moreover, the use of certain cationic direct dyes may be reflected by a reduction in the working qualities of the shampoos used after coloration, especially as regards the duration of the lather.

The present invention is thus directed to a process for inhibiting the phenomenon of bleeding of color from hair fibers during shampooing.

SUMMARY OF THE INVENTION

In order to achieve these and other advantages, the present invention is drawn to a process for inhibiting dyed hair fibers from losing their color during shampooing involving contacting the dyed hair fibers with a composition containing:
  (a) at least one polyamine compound having at least two amino groups;
  (b) at least one anionic silicone; and
  (c) optionally, at least one surfactant, and
    wherein (a) is present in an amount sufficient to inhibit the dyed hair fibers from losing their color during shampooing.

DETAILED DESCRIPTION

Other than in the operating examples, or where otherwise indicated, all numbers expressing quantities of ingredients and/or reaction conditions are to be understood as being modified in all instances by the term "about".

"Amino groups" as defined herein includes primary amino groups, secondary amino groups, and tertiary amino groups, and further includes amino groups which are terminal, pendant, and intercalated in a skeleton of the at least one polyamine compound, but does not, for example, include quaternary amino groups, amido groups, imino groups, nitrilo groups, or heteroatom analogs of any of the foregoing.

"At least one" as used herein means one or more and thus includes individual components as well as mixtures/combinations.

The at least one polyamine compound of the present invention comprises at least two amino groups, preferably at least three amino groups, more preferably at least four amino groups, more preferably at least five amino groups, more preferably at least six amino groups, more preferably at least seven amino groups, more preferably at least eight amino groups, more preferably at least nine amino groups, and more preferably at least ten amino groups.

In one embodiment of the present invention, the at least one polyamine compound may, for example, be chosen from aminated polysaccharides comprising at least two amino groups, such as, for example, hydrolysates (through chemical and/or enzymatic process) of aminated polysaccharides comprising greater than two amino groups. In one embodiment, the at least one polyamine compound may, for example, be chosen from polymers. Suitable polymers for use as the at least one amine compound are polymers comprising at least two amino groups as defined herein. Non-limiting examples of suitable polymers include homopolymers comprising at least two amino groups, copolymers comprising at least two amino groups, and terpolymers comprising at least two amino groups. Thus, the at least one polyamine compound comprising at least two amino groups may be chosen from, for example, polymers comprising at least two amino groups formed from (i) at least one monomer unit comprising at least one amino group as defined herein, and, optionally, (ii) at least one additional monomer unit different from the at least one monomer (i); and polymers comprising at least two amino groups formed from (i) at least one monomer comprising at least two amino groups as defined herein, and, optionally, (ii) at least one additional monomer unit different from the at least one monomer (i). According to the present invention, the at least one additional monomer different from the at least one monomer (i) may or may not comprise at least one amino group as defined herein. A particularly preferred polyamine polymer is chitosan.

In one embodiment of the present invention, the at least one polyamine compound is chosen from polyamines. As used herein, "polyamines" comprise at least two repeating units, wherein each unit comprises at least one amino group as defined herein. In one embodiment, polyamines are chosen from polyethyleneimines. Polyethyleneimines suitable for use in the compositions of the present invention may optionally be substituted. Non-limiting examples of polyethyleneimines which may be used in the composition according to the present invention are the Lupasol™ products commercially available from BASF. Suitable examples of Lupasol™ polyethyleneimines include Lupasol™ PS, Lupasol PL, Lupasol™ PR8515, Lupasol™ G20, Lupasol™ G35 as well as Lupasol™ SC® Polythyleneimine Reaction Products (such as Lupasol™ SC-61B®, Lupasol™ SC-62J®, and Lupasol™ SC-86X®). Other non-limiting examples of polyethyleneimines which may be used in the composition according to the present invention are the Epomin™ products commercially available from Aceto. Suitable examples of Epomin™ polyethyleneimines include Epomin™ SP-006, Epomin™ SP-012, Epomin™ SP-018, and Epomin™ P-1000.

Polyamines suitable for use in the present invention may also be chosen from polyvinylamines. Examples thereof include Lupamines® 9095, 9030, 9010, 5095, 1595 from BASF.

The polyamine compounds can also be substituted. An example of such a compound is PEG-15 Cocopolyamine from Cognis.

In another embodiment, the at least one polyamine compound comprising at least two amino groups is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, $8^{th}$ edition, vol. 2, (2000). In one embodiment, the at least one polyamine compound comprising at least two amino groups is chosen from wheat protein, soy protein, oat protein, collagen, and keratin protein.

In one embodiment, the at least one polyamine compound comprising at least two amino groups is not chosen from proteins and protein derivatives. In one embodiment, the at least one polyamine compound comprising at least two amino groups is not chosen from compounds comprising lysine, compounds comprising arginine, and compounds comprising histidine. In one embodiment, the at least one polyamine compound comprising at least two amino groups is chosen from compounds comprising lysine, compounds comprising arginine, compounds comprising histidine, and compounds comprising hydroxylysine.

In the present invention, the at least one polyamine compound is employed in an amount sufficient to inhibit dyed hair fibers from losing their color during shampooing and/or inhibit hair fibers, in general, from appearing frizzy, especially when exposed to high humidity. Typically, it will be present in an amount of from greater than 0% to 30% by weight, preferably from 5% to 20% by weight, and more preferably from 5% to 10% by weight, based on the weight of the composition as a whole.

In general, non-limiting examples of anionic silicones which may be used in the process of the present invention include silicone carboxylates, silicone phosphates, silicone sulfates, silicone sulfosuccinates, and silicone sulfonates.

Suitable silicone carboxylates may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the at least one silicone compound comprising at least one carboxylic acid group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the at least one silicone compound comprising at least one carboxylic acid group is chosen from silicone compounds of formula (I) and salts thereof:

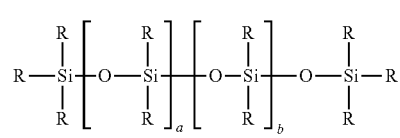

wherein: a is an integer ranging from 1 to 100; b is an integer ranging from 0 to 500; R, which may be identical or different, are each chosen from optionally substituted hydrocarbon groups comprising from 1 to 9 carbon atoms, optionally substituted phenyl groups, and groups of formula (II):

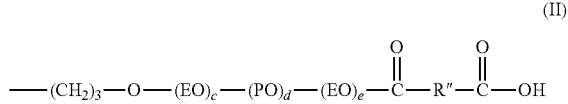

wherein: c, d, and e, which may be identical or different, are each integers ranging from 0 to 20; EO is an ethylene oxide group; PO is a propylene oxide group; and R″ is chosen from optionally substituted divalent hydrocarbons, such as alkylene groups and alkenylene groups comprising from 2 to 22 carbon atoms, and optionally substituted divalent aromatic groups, such as groups of formula (III):

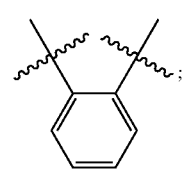

and groups of formula (IV):

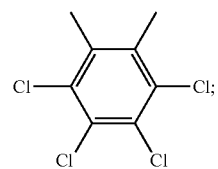

with the proviso that at least one of the R groups is chosen from groups of formula (II) and with the further proviso that when only one of the R groups is chosen from groups of formula (II), the other R groups are not all methyl groups.

Non-limiting examples of the at least one silicone compound include those commercially available from Noveon under the name Ultrasil® CA-1 Silicone and Ultrasil® CA-2 Silicone, both of which correspond to formula (V) below. This silicone carboxylate is sold in the free acid form as an emulsifier and dispersing aid for complexing fatty cationic amines and quaternary amines. Thus, in one embodiment, the at least one silicone compound is chosen from silicone compounds of formula (V) and salts thereof:

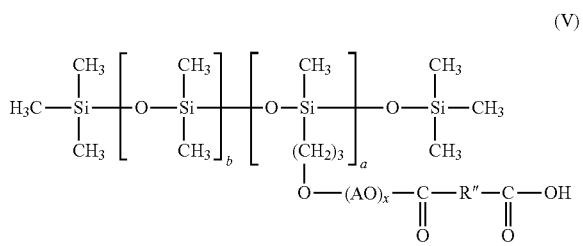

wherein: a is an integer ranging from 1 to 100; b is an integer ranging from 0 to 500; AO is chosen from groups of formula (VI):

wherein: c, d, and e, which may be identical or different, are each integers ranging from 0 to 20; EO is an ethylene oxide group; and PO is a propylene oxide group; x is an integer ranging from 0 to 60; R″ is chosen from optionally substituted divalent hydrocarbons, such as alkylene groups and alkenylene groups comprising from 2 to 22 carbon atoms, and optionally substituted divalent aromatic groups, such as groups of formula (III):

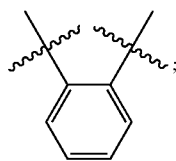

and groups of formula (IV):

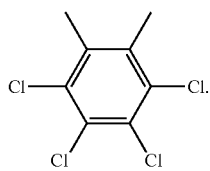

Non-limiting examples of the at least one silicone compound include those described in U.S. Pat. Nos. 5,248,783 and 5,739,371, the disclosures of which are incorporated herein by reference, and which are silicone compounds of formula (I).

Suitable silicone phosphates may be chosen from water-soluble silicone compounds comprising at least one phosphate group, oil soluble silicone compounds comprising at least one phosphate group, water-dispersible silicone compounds comprising at least one phosphate group, and silicone compounds comprising at least one phosphate group which are soluble in organic solvents.

In one embodiment, the at least one silicone compound comprising at least one phosphate group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups ("EO"=—$CH_2$—$CH_2$—O—) and propylene oxide groups ("PO"=$C_3H_6O$).

The at least one phosphate group may be chosen from terminal phosphate groups and pendant phosphate groups. Further, the at least one phosphate group may be chosen from groups of formula —O—P(O)(OH)$_2$, groups of formula —O—P(O)(OH)(OR), and groups of formula —O—P(O)(OR)$_2$, wherein R may be chosen from H, inorganic cations, and organic cations. Non-limiting examples of inorganic cations include alkali metals, such as, for example, potassium lithium, and sodium. A non-limiting example of organic cations is at least one additional silicone compound which may be identical to or different from the at least one silicone compound bonded to the other oxygen of the phosphate group.

In one embodiment, the at least one silicone compound comprising at least one phosphate group is chosen from silicone compounds of formula (VII):

wherein $R^1$, which may be identical or different, are each chosen from H, organic cations, inorganic cations, optionally substituted hydrocarbons (such as alkyl groups and alkenyl groups comprising from 1 to 22 carbon atoms), optionally substituted aromatic groups; groups of formula (VIII) and salts thereof:

wherein: c and d, which may be identical or different, are each integers ranging from 0 to 20; e is an integer ranging from 0 to 19; and x is an integer ranging from 0 to 21; groups of formula (IX) and salts thereof:

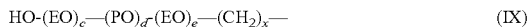

wherein: c, d, and e, which may be identical or different, are each integers ranging from 0 to 20; and x is an integer ranging from 0 to 21; and groups of formula (X) and salts thereof:

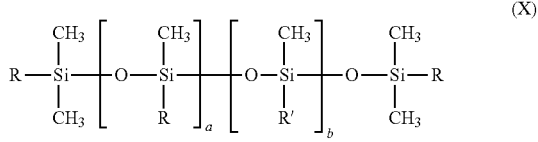

wherein: a is an integer ranging from 0 to 200; b is an integer ranging from 0 to 200; R', which may be identical or different, are each chosen from optionally substituted hydrocarbons, such as alkyl groups and alkenyl groups comprising from 1 to 22 carbon atoms, optionally substituted aromatic groups, groups of formula (III) as defined above and salts thereof; and R, which may be identical or different, are each chosen from optionally substituted hydrocarbons, such as alkyl groups and alkenyl groups comprising from 1 to 22 carbon atoms, optionally substituted aromatic groups, optionally substituted divalent hydrocarbons, such as alkylene groups and alkenylene groups comprising from 1 to 22 carbon atoms, optionally substituted divalent aromatic groups, groups of formula (VIII) as defined above and salts thereof, and groups of formula (XI):

wherein:

the (CH$_2$)$_3$ end is bonded to the silicon of the compound of formula (X) and the (EO) or (PO) end, if present, is bonded to the oxygen of the compound of formula (I); c, d, and e, which may be identical or different, are each integers ranging from 0 to 20; EO is an ethylene oxide group; and PO is a propylene oxide group; and with the proviso that at least one R is chosen from groups of formula (XI) and salts thereof; and with the further proviso that at least one R$^1$ is chosen from groups of formula (X) and salts thereof and at least one other R$^1$ is chosen from H, organic cations, and inorganic cations.

Non-limiting examples of the inorganic cations include alkali metals, such as potassium, lithium, and sodium. Non-limiting examples of the at least one silicone compound include those commercially available from Phoenix Chemical, Inc. of New Jersey under the name of Pecosil®, such as Pecosil® PS-100, Pecosil® PS-112, Pecosil® PS-150, Pecosil® PS-200, Pecosil® WDS-100, Pecosil® WDS-200, Pecosil® PS-100 B, and Pecosil® PS-100 K and those commercially available from Siltech under the name Silphos A-100 and Silphos A-150. Other non-limiting examples of the at least one silicone compound include those described in U.S. Pat. Nos. 5,070,171, 5,093,452, and 5,149,765 the disclosures of which are incorporated herein by reference.

Suitable silicone sulfates for use in the present invention include those represented by formula XII:

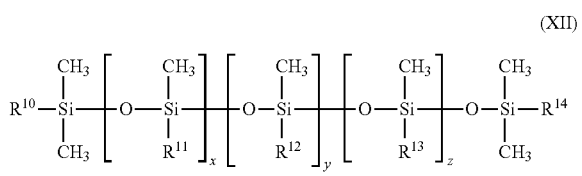

(XII)

wherein R$^{11}$ is selected from lower alkyl having one to eight carbon atoms or phenyl, R$^{12}$ is —(CH$_2$)$_3$—O-(EO)$_x$—(PO)$_y$-(EO)$_z$—SO$_3^{31}$-M$^+$ wherein M is a cation and is selected from Na, K, Li, or NH$_4$; x, y and z are integers independently ranging from 0 to 100; R$^{13}$ is —(CH$_2$)$_3$—O-(EO)$_x$—(PO)$_y$-(EO)$_z$—H; R$^{14}$ is methyl or hydroxyl; a$^1$ and c$^1$ are independently integers ranging from 0 to 50; b$^1$ is an integer ranging from 1 to 50. An example thereof is Ultrasil SA-1 silicone commercially available from Noveon.

Suitable silicone sulfosuccinates which may be employed include, but are not limited to, those corresponding to formula XIII:

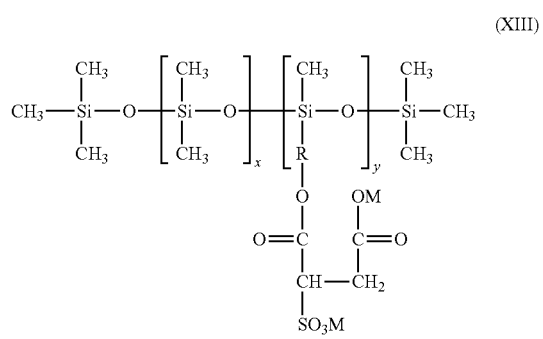

(XIII)

wherein R represents a divalent radical selected from

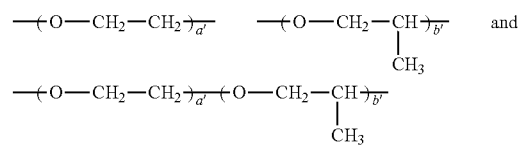

wherein a' and b' range from 0 to 30; x and y are such that the molecular weight ranges from 700 to 1600, and M is an alkali metal such as sodium or potassium, or an ammonium group.

A particularly preferred anionic silicone is Dimethicone PEG-8 phosphate, commercially available from Noveon under the trade name Ultrasil PE-100.

The anionic silicone may be employed in an amount ranging from greater than 0 to 50% by weight, preferably from 5 to 30% by weight, and more preferably from 5 to 15% by weight, based on the weight of the composition as a whole.

It may also be desirable to employ various auxiliary ingredients, depending on the type of hair care composition being formulated, i.e., shampoo, conditioner, leave-on/deep treatment, and the like.

For example, when formulating a shampoo, a detersive surfactant will typically be employed in order to impart cleaning capabilities to the compositions. Examples of suitable detersive surfactants include nonionic surfactants, anionic surfactants, amphoteric/zwitterionic surfactants.

Suitable nonionic surfactants are any suitable nonionic surfactants that have an HLB of from about 3 to about 14. The abbreviation "HLB" stands for hydrophilic lipophilic balance. Examples of suitable nonionic surfactants include, but are not limited to, fatty acid esters and alkoxylated, particularly ethoxylated, fatty acid esters of polyhydric alcohols such as glycerols and sorbitol, for example, polyoxyethylene monolaurate, polyoxyethylene monooleate, polyoxyethylene monostearate, sorbitan monolaurate, sorbitan trioleate, generally with a degree of ethoxylation of from about 20 to about 85; mono- and di-alkanolamides, such as the N-acyl derivatives of mono- and di-ethanol amines, and polyethoxylated monoalkanolamides; amine oxides, such as cocoamidopropyl dimethylamine oxides, coco bis-2-hydroxyethyl amine oxides and lauryl dimmethylamine oxide; ethoxylated alkanolamides; ethoxylated oils and fats such as ethoxylated lanolins; and ethoxylated alkylphenols, such as Nonoxynol.

Suitable anionic surfactants include, for example, the following: the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about C$_{12}$ to C$_{18}$ alkyl or alkenyl groups. Particularly preferred are the salts of lauryl sulfates and lauryl ether sulfates the latter having an average level of ethoxylation of 1-3.

Amphoteric/zwitterionic surfactants belong to the category of surface active chemicals that possess a positive and a negative charge in the same molecule and behave as a cation or an anion depending on the pH of the medium. In general, the positive charge is located on a nitrogen atom while the negative charge is carried by a carboxyl or sulfonate group.

There are a large number of amphoteric surfactants that are suitable for use in this invention. They include, for example, lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, cocoamphopropylsulfonate.

The amphoteric surfactants presently preferred for use in this invention are: cocamidopropyl betaine, coco-betaine, stearyl betaine, cocoamphocarboxyglycinate, cocoamphodipropionate, and stearoamphoglycinate.

The detersive surfactant may be employed in an amount of from greater than 0 to 80% by weight, preferably from 5 to 50% by weight, and more preferably from 15 to 30% by weight, based on the weight of the composition as a whole.

Conditioning agents may also be employed in order to impart added conditioning benefits to the composition. The conditioning agents useful in the present invention are those which are dispersible in water and typically may be chosen from cationic surfactants, silicone compounds, polyalkylene glycols and mixtures thereof, preferably mono long-chain ammonium compounds, hydrophilically substituted cationic surfactants, hydrophilically substituted silicone compounds, polyalkylene glycols, and mixtures thereof.

The type of conditioning agent selected depends on the desired characteristics of the product. Highly water soluble conditioning agents are typically used. A combination of conditioning agents is preferably used to provide benefits provided by the different conditioning agents. Conditioning agents which are less water soluble can be used in combination with highly water soluble conditioning agents.

Cationic surfactants may be used as conditioning agents herein. Suitable cationic surfactants useful herein include, but are not limited to, those generally described as mono long-chain ammonium compounds. Nonlimiting examples of such cationic surfactants include: cetyl trimethyl ammonium chloride available, for example, with trade name CA-2350 from Nikko Chemicals and CTAC 30KC available from KCI, stearyl trimethyl ammonium chloride with trade name Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl(myristylacetate)ammonium chloride, and N-(stearoyl colamino formyl methy)pyridinium chloride.

Also preferred are hydrophilically substituted cationic surfactants in which at least one of the substituents contain one or more aromatic, ether, ester, amido, or amino moieties present as substituents or as linkages in the radical chain. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, alkyl amidopropyl trimonium salt, polyoxyethylene alkyl ammonium salt, and mixtures thereof; for example, commercially available under the following trade names; VARISOFT 110, VARISOFT PATC, VARIQUAT K1215 and 638 from Witco Chemical, ETHOQUAD 18/25, ETHOQUAD O/12PG, ETHOQUAD C/25, and ETHOQUAD S/25 from Akzo, DEHYQUART SP from Cognis, and MONAQUAT ISEIS, and MONAQUAT SL-5 available from Uniqema.

The polyalkylene glycols useful herein as conditioning agents include those which are soluble or dispersible in water. Polyethylene glycols are preferred.

Polyalkylene glycols having a molecular weight of more than about 100 are useful herein. Ethylene oxide polymers are preferred in view of their generally good water solubility, dispersibility, and transparency. Polyethylene-polypropylene glycols and polyoxyethylene-polyoxypropylene copolymer polymers having good dispersibility and transparency may also be useful.

The composition of the present invention may also comprise additives, for instance those chosen from the non-exhaustive list such as reducing agents, antioxidants, sequestering agents, softeners, antifoams, moisturizers, emollients, basifying agents, plasticizers, sunscreens, direct dyes or oxidation dyes, pigments, mineral fillers, clays, colloidal minerals, nacres, nacreous agents, fragrances, peptizers, preserving agents, fixing or non-fixing polymers, proteins, vitamins, antidandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, oxyethylenated or non-oxyethylenated waxes, paraffins, fatty acids, associative or non-associative thickening polymers, fatty amides, fatty esters, fatty alcohols, and the like.

The present invention will be better understood from the examples which follow, all of which are intended for illustrative purposes only and are not meant to unduly limit the scope of the invention in any way.

EXAMPLES

General Procedure:

Bleached hair swatches were dyed with commercially available colors. Following the coloring process, the initial L*a*b* values of the swatches were obtained. The colored swatches were swirled in a beaker containing 50 g of a polyamine: silicone phosphate solution and blown dry. Swatches were shampooed three consecutive times with a 10% SLES-2 solution (pH 6.07). Specifically, 0.4 g of SLES-2 solution per 1 g of hair was applied, massaged into the swatch for 15 seconds, and rinsed with warm water for 10 seconds. Following the third shampoo, swatches were blown dry. Swatches were retreated and shampooed in the same manner, for a total of 2 treatments and 6 shampoos. Final colorimetric data were obtained and the ΔE* value, representing the total color change was calculated using the following formula:

$$\Delta E^* = [(\Delta a^*)^2 + (\Delta b^*)^2 + (\Delta c^*)^2]^{1/2}$$

In all polyamine+anionic silicone solutions, the reported concentration is percent active.

Example 1

Effectiveness of Polyamines/Silicone Phosphate Solutions as Leave On Treatments

Following the General Procedure, hair swatches were dyed with Redken Color Fusion Hi-Fusion R containing chromatic dyes. The chromatic coloration was mixed in a 1:1 ratio with Redken Pro-oxide 20 Volume Cream Developer and remained on the hair for 30 minutes.

Swatches were treated in triplicate with one of the following polyamine: anionic silicone solutions:

A: 1.0% polyethylenimine (PEI) and 1.7% dimethicone PEG-8 phoshate, pH 5
B: 2.0% PEI and 1.7% dimethicone PEG-8 phosphate, pH 5
C: 2.0% PEI and 1.7% dimethicone PEG-8 phosphate, pH 7
D: 1.0% PEI and 3.4% dimethicone PEG-8 phosphate, pH 5
E: 0.5% Chitosan and 1.5% dimethicone PEG-8 phosphate, pH 5
F: 1.0% Chitosan and 3% dimethicone PEG-8 phosphate, pH 5
G: 2.0% polyvinylamine (Lupamin 9095) and 2.75% dimethicone PEG-8 phosphate, pH 5
H: 2.0% polyvinylamine (Lupamin 9030) and 2.75% dimethicone PEG-8 phosphate, pH 5
I: 2.0% polyvinylamine (Lupamin 9010) and 2.75% dimethicone PEG-8 phosphate, pH 5
Water, instead of the polyamine: anionic silicone solution was used as the control After 2 treatments and 6 shampoos with the various polyamine/anionic silicone solutions, there was a statistically significant improvement in color retention compared with those swatches treated with water. Table I displays the resulting ΔE* values

TABLE I

Total Color Change of Treated Hair After 6 Shampoos

| Sample | ΔE* value |
|--------|-----------|
| A | 18.65 |
| B | 16.70 |
| C | 15.12 |
| D | 19.35 |
| E | 22.75 |
| F | 16.62 |
| G | 20.17 |
| H | 23.57 |
| I | 25.93 |
| Water | 28.85 |

Example 2

Effectiveness of Polyamines/Silicone Phosphate/Nonionic Surfactant Solution as a Leave On Treatment Following the General Procedure, hair swatches were dyed with Paul Michell Inkworks, Matrix Prizms Light Auburn, Redken Color Fusion Hi-Fusion R, Redken Color Fusion 5Vr containing acid dyes, basic/Arianor dyes, chromatic dyes, oxidative dyes, respectively. The chromatic and oxidative colorations were mixed in a 1:1 ratio with Redken Pro-oxide 20 Volume Cream Developer and remained on the hair for 30 minutes, while the acid and basic colorations were applied to the hair as is and remained on the hair at least 15 minutes.

Swatches were treated in triplicate with one of the following polyamine: anionic silicone solutions:
J: 10% Polysorbate 80 (control)
K: 10% Polysorbate 80 with 2.0% PEI and 1.7% Dimethicone PEG-8 phosphate After at least 2 treatments and 6 shampoos with the 10% Polysorbate 80 solution containing PEI and Dimethicone PEG-8 phosphate on various dye types, there was a statistically significant improvement in color retention compared with those swatches treated with 10% Polysorbate 80 (control). Table II displays the resulting ΔE* values.

TABLE II

Total Color Change of Treated Hair After At Least 6 Shampoos

| Coloration | Sample | ΔE* value |
|------------|--------|-----------|
| Acid | J | 7.33 |
|  | K | 4.81 |
| Basic | J | 15.40 |
|  | K | 11.03 |
| Chromatic | J | 24.07 |
|  | K | 9.68 |
| Oxidative | J | 21.37 |
|  | K | 16.75 |

Example 3

Effectiveness of Polyamines/Silicone Phosphate in Anionic Shampoo

Following the General Procedure, hair swatches were dyed with Redken Color Fusion Hi-Fusion R and Redken Shades EQ Rocketfire containing chromatic dyes and direct dyes/oxidative dyes, respectively. The chromatic coloration was mixed in a 1:1 ratio with Redken Pro-oxide 20 Volume Cream Developer and remained on the hair for 30 minutes. The direct and oxidative coloration was mixed with Redken Shades EQ Processing Solution in a 1:1 ratio and remained on the hair 20 minutes.

Swatches were treated in triplicate with one of the following anionic shampoos 6 times:
L: Shampoo control containing 4.2% SLES-2 and 9.8% Laureth-5 Carboxylic Acid
M: Shampoo containing 4.2% SLES-2 and 9.8% Laureth-5 Carboxylic Acid with 2.0% PEI and 1.7% Dimethicone PEG-8 phosphate After 6 shampoos with the anionic shampoo containing PEI and Dimethicone PEG-8 phosphate on hair swatches colored with various dye types, there was a statistically significant improvement in color retention compared with those swatches treated with the Shampoo control. Table III displays the resulting ΔE* values.

TABLE III

Total Color Change of Treated Hair After 6 Shampoos

| Coloration | Sample | ΔE* value |
|------------|--------|-----------|
| Chromatic | L | 23.02 |
|  | M | 9.11 |
| Direct Dyes/Oxidative | L | 16.53 |
|  | M | 15.31 |

Example 4

Effectiveness of Polyamines/Silicone Phosphate in Anionic/Amphoteric Shampoo

Following the General Procedure, hair swatches were dyed with Paul Michell Inkworks, Matrix Prizms Light Auburn, Redken Color Fusion Hi-Fusion R, Redken Color Fusion 5Vr as described above.

Swatches were treated in triplicate with one of the following anionic shampoos for at least 7 times:

N: Shampoo control containing 5% Ammonium Laureth Sulfate and 10% Cocamidopropyl Hydroxysultaine O: Shampoo containing 5% Ammonium Laureth Sulfate and 10% Cocamidopropyl Hydroxysultaine with 1.25% PEI and 0.5% Dimethicone PEG-8 phosphate After at least 7 shampoos with the Anionic/Amphoteric Shampoo containing PEI and Dimethicone PEG-8 phosphate on hair swatches colored with various dye types, there was a statistically significant improvement in color retention compared with those swatches treated with the Shampoo control. Table IV displays the resulting ΔE* values.

TABLE IV

Total Color Change of Treated Hair After 7 Shampoos

| Coloration | Sample | ΔE* value |
|---|---|---|
| Acid | N | 10.61 |
|  | O | 3.13 |
| Basic | N | 14.76 |
|  | O | 5.51 |
| Chromatic | N | 11.20 |
|  | O | 6.38 |
| Oxidative | N | 15.03 |
|  | O | 11.82 |

What is claimed is:

1. A process for inhibiting dyed hair fibers from losing their color during shampooing, said process comprising: contacting the dyed hair fibers with a composition containing:
   (a) at least one polyamine compound having at least two amino groups selected from the group consisting of polyvinylamine and polyethyleneimine;
   (b) at least one anionic silicone selected from the group consisting of dimethicone PEG-7 phosphate and dimethicone PEG-8 phosphate; and
   (c) optionally, at least one surfactant, and
   wherein (a) is present in the composition in an amount sufficient to inhibit the dyed hair fibers from losing their color during shampooing.

2. The process of claim 1 wherein (a) is a polyethyleneimine.

3. The process of claim 1 wherein (a) is a polyvinylamine.

4. The process of claim 1 wherein (a) is present in an amount of from greater than 0 to about 30% by weight, based on the weight of the composition.

5. The process of claim 1 wherein (a) is present in an amount of from about 5% to about 10% by weight, based on the weight of the composition.

6. The process of claim 1 wherein (b) is present in an amount of from greater than 0 to about 50% by weight, based on the weight of the composition.

7. The process of claim 1 wherein (b) is present in an amount of from greater than 0% to about 15% by weight, based on the weight of the composition.

8. The process of claim 1 wherein the composition comprises an anionic surfactant.

9. The process of claim 1 wherein (c) is present in an amount of from greater than 0% to about 80% by weight, based on the weight of the composition.

10. The process of claim 1 wherein the composition is a shampoo.

11. The process of claim 1 wherein the composition is a hair conditioning product.

12. The process of claim 1 wherein the anionic silicone comprises dimethicone PEG-8 phosphate.

13. The process of claim 1, wherein the composition comprises a non-ionic surfactant.

14. The process of claim 1, wherein the at least one polyamine compound having at least two amino groups is a polyethyleneimine and the at least one anionic silicone is dimethicone PEG-8 phosphate.

15. The process of claim 1, wherein the at least one polyamine compound having at least two amino groups is a polyvinylamine and the at least one anionic silicone is dimethicone PEG-8 phosphate.

* * * * *